United States Patent
Brockway et al.

(10) Patent No.: US 9,414,758 B1
(45) Date of Patent: Aug. 16, 2016

(54) APPARATUS, SYSTEM AND METHODS FOR SENSING AND PROCESSING PHYSIOLOGICAL SIGNALS

(75) Inventors: Brian Brockway, St. Paul, MN (US); Marina Brockway, St. Paul, MN (US); Anna M. Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 1000 days.

(21) Appl. No.: 13/349,314

(22) Filed: Jan. 12, 2012

Related U.S. Application Data

(60) Provisional application No. 61/432,095, filed on Jan. 12, 2011.

(51) Int. Cl.
*A61B 5/0408* (2006.01)
*A61B 5/00* (2006.01)

(52) U.S. Cl.
CPC .............. *A61B 5/0408* (2013.01); *A61B 5/6801* (2013.01); *A61B 5/726* (2013.01)

(58) Field of Classification Search
CPC .... A61B 5/04; A61B 5/04004; A61B 5/0408; A61B 5/0492; A61B 5/6801; A61B 5/6804; A61B 5/6805; A61B 5/683; A61B 5/68939; A61B 2562/028; A61B 2562/0285; A61B 5/72; A61B 5/7207; A61B 5/721; A61B 5/7228; A61B 5/726
USPC ................. 600/372, 382, 384, 395, 509, 546; 442/111
See application file for complete search history.

(56) References Cited

U.S. PATENT DOCUMENTS

| | | | |
|---|---|---|---|
| 5,090,418 A | 2/1992 | Squires et al. | |
| 5,331,959 A * | 7/1994 | Imran | 600/383 |
| 5,521,851 A | 5/1996 | Wei et al. | |
| 5,792,065 A | 8/1998 | Xue et al. | |
| 5,817,027 A | 10/1998 | Arand et al. | |
| 5,827,195 A | 10/1998 | Lander | |
| 5,987,352 A | 11/1999 | Klein et al. | |
| 6,389,308 B1 | 5/2002 | Shusterman | |
| 6,589,189 B2 | 7/2003 | Meyerson et al. | |
| 6,690,959 B2 | 2/2004 | Thompson | |
| 6,701,170 B2 | 3/2004 | Stetson | |
| 6,822,564 B2 | 11/2004 | Al-Ali | |
| 7,096,060 B2 | 8/2006 | Arand et al. | |
| 7,115,096 B2 | 10/2006 | Siejko et al. | |

(Continued)

FOREIGN PATENT DOCUMENTS

WO 2013/043157 A2 3/2013

OTHER PUBLICATIONS

Allen, et al. "Honey Carbon: A Review of Graphene" 30 Chem. Rev. 110:132-145 (2010).*

(Continued)

*Primary Examiner* — Lee S Cohen
*Assistant Examiner* — Erin M Cardinal
(74) *Attorney, Agent, or Firm* — Crawford Maunu PLLC

(57) ABSTRACT

Monitoring of physiological signals is effected. In accordance with one or more embodiments, an apparatus, system and/or method is directed to sensing physiological signals such as ECG signals. A skin-contacting electrode apparatus includes an electrically conductive sheet having a conductive surface configured and arranged to contact a subject's skin, and conductive flexible microfibers extending from the conductive surface and configured and arranged to protrude into skin pores and sense an ECG signal.

24 Claims, 8 Drawing Sheets

(56) References Cited

U.S. PATENT DOCUMENTS

| | | | |
|---|---|---|---|
| 7,236,819 | B2 | 6/2007 | Brockway et al. |
| 7,272,265 | B2 | 9/2007 | Kouri et al. |
| 7,376,453 | B1 | 5/2008 | Diab et al. |
| 7,627,369 | B2 | 12/2009 | Hunt |
| 7,672,717 | B1 | 3/2010 | Zikov et al. |
| 7,840,259 | B2 | 11/2010 | Xue et al. |
| 8,086,304 | B2 | 12/2011 | Brockway et al. |
| 8,201,330 | B1 | 6/2012 | Rood et al. |
| 8,214,007 | B2 | 7/2012 | Baker et al. |
| 8,271,073 | B2 | 9/2012 | Zhang et al. |
| 8,348,852 | B2 | 1/2013 | Bauer et al. |
| 8,460,189 | B2 | 6/2013 | Libbus et al. |
| 8,478,389 | B1 | 7/2013 | Brockway et al. |
| 8,543,195 | B1* | 9/2013 | Brockway et al. ............ 600/509 |
| 8,608,984 | B1* | 12/2013 | Taranekar et al. ............ 252/511 |
| 2002/0077536 | A1* | 6/2002 | Diab et al. .................... 600/323 |
| 2004/0111141 | A1* | 6/2004 | Brabec et al. ................. 607/119 |
| 2005/0010120 | A1 | 1/2005 | Jung et al. |
| 2005/0075708 | A1* | 4/2005 | O'Brien et al. ............... 607/116 |
| 2005/0203604 | A1* | 9/2005 | Brabec et al. ................. 607/122 |
| 2005/0234361 | A1 | 10/2005 | Holland |
| 2005/0283090 | A1 | 12/2005 | Wells |
| 2007/0060815 | A1* | 3/2007 | Martin et al. ................. 600/372 |
| 2007/0219453 | A1 | 9/2007 | Kremliovsky et al. |
| 2007/0219455 | A1 | 9/2007 | Wong et al. |
| 2007/0260151 | A1 | 11/2007 | Clifford |
| 2007/0265508 | A1 | 11/2007 | Sheikhzadeh-Nadjar et al. |
| 2008/0065158 | A1 | 3/2008 | Ben-Ezra et al. |
| 2008/0097280 | A1* | 4/2008 | Martin et al. .................. 604/21 |
| 2008/0097537 | A1 | 4/2008 | Duann et al. |
| 2008/0183093 | A1 | 7/2008 | Duann et al. |
| 2008/0200832 | A1 | 8/2008 | Stone |
| 2008/0287770 | A1* | 11/2008 | Kurzweil et al. ............. 600/388 |
| 2009/0069703 | A1 | 3/2009 | Takla et al. |
| 2009/0222262 | A1 | 9/2009 | Kim et al. |
| 2011/0046461 | A1* | 2/2011 | McKenna ..................... 600/323 |
| 2012/0165691 | A1 | 6/2012 | Ting et al. |
| 2012/0197144 | A1 | 8/2012 | Christ et al. |
| 2012/0232417 | A1 | 9/2012 | Zhang |
| 2013/0019383 | A1* | 1/2013 | Korkala et al. .................... 2/338 |
| 2013/0109937 | A1 | 5/2013 | Banet et al. |
| 2014/0005988 | A1 | 1/2014 | Brockway |
| 2014/0135608 | A1* | 5/2014 | Gazzoni et al. ............... 600/395 |

OTHER PUBLICATIONS

Igarashi, et al. "The Appearance of Human Skin" Technical Report: CUCS-024-05, Dept. of Comp. Sci., Columbia Univ. NY (2005).*

Pan et al. "Accurate Removal of Baseline Wander in ECG Using Empirical Mode Decomposition" Proceedings of NFSI & ICFBI pp. 177-180 (2007).*

B. Windrow, et al., "Adaptive noise cancelling: principals and applications," IEEE Proc., vol. 63, No. 12, pp. 1692-1716, Dec. 1975.

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Y. Pati, R. Rezaiifar and P. Krishnaprasad, "Orthogonal Matching Pursuit: Recursive Function Approximation with Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution," Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J._Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvärinen, "New Approximations of Differential Entropy for Independent Component Analysis and Projection Pursuit," in Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157— 192 (1999).

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

C. Taswell, "The What, How, and Why of Wavelet Shrinkage Denoising," Computing in Science and Engineering, vol. 2, No. 3, pp. 12-19 (2000).

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

M. Brennan, M. Palaniswami, and P. Kamen. Do Existing Measures of Poincare Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

M. Costa, A. L. Goldberger, and C.-K. Peng, Multiscale Entropy Analysis of Complex Physiologic Time Series, Phys. Rev. Lett. 89, 6, (2002).

(56) References Cited

OTHER PUBLICATIONS

B. U. Kohler, C. Hennig, R. Orglmeister. The principles of software QRS detection. IEEE Engineering in Medicine and Biology Magazine, vol. 21, No. 1. (2002), pp. 42-57.

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

K. Oweiss , A. Mason , Y. Suhail , A. Kamboh and K. Thomson, "A Scalable Wavelet Transform VLSI Architecture for Real-Time Signal Processing in High-Density Intra-Cortical Implants" , IEEE Trans. Circuits Syst. I, vol. 54, No. 6, pp. 1266-1278 (Jun. 2007).

K. Todros and J. Tabrikian, "Blind Separation of Independent Sources Using Gaussian Mixture Model," IEEE Transactions on Signal Processing, vol. 55, No. 7, pp. 3645-3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

X. Li, X. Yao, J. J Fox, and J. Jefferys, "Interaction Dynamics of Neuronal Oscillations Analysed Using Wavelet Transforms," Journal of Neuroscience Methods 160, pp. 178-185 (2007).

M. Malik, K. Hnatkova, T. Novotny, G Schmidt Subject-specific profiles of QT/RR hysteresis. Am J Physiol Heart Circ Physiol 295:H2356-H2363, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

Attila S. Farkas. et. al. Biomarkers and endogenous determinants of dofetilide-induced torsades de pointes in $\alpha 1$-adrenoceptor-stimulated, anaesthetized rabbits. British Journal of Pharmacology. vol. 161, Issue 7, pp. 1477-1495, Dec. 2010.

Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

Kellermann, et al.,"A mobile phone based alarm system for supervising vital parameters in free moving rats," BMC Research Notes 2012, 5:119, Feb. 23, 2012.

\* cited by examiner

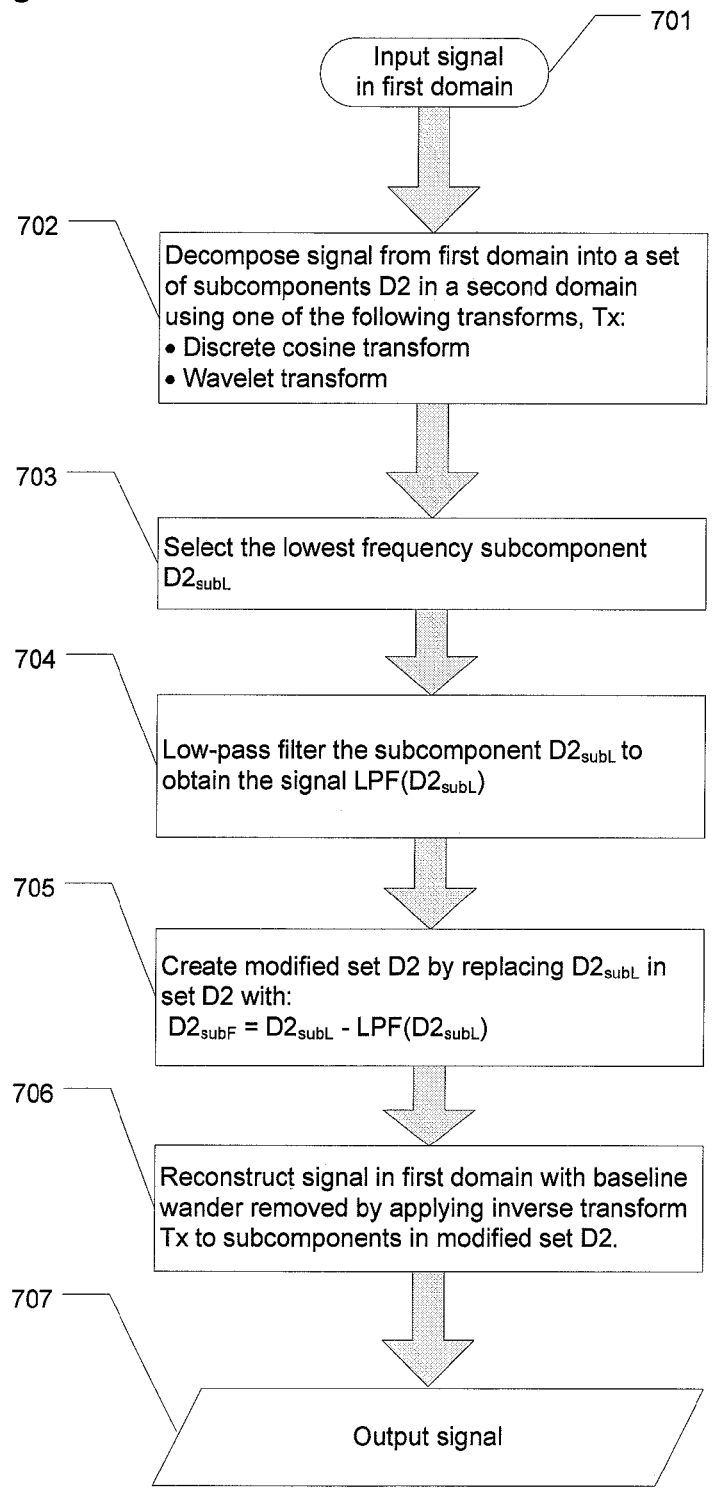

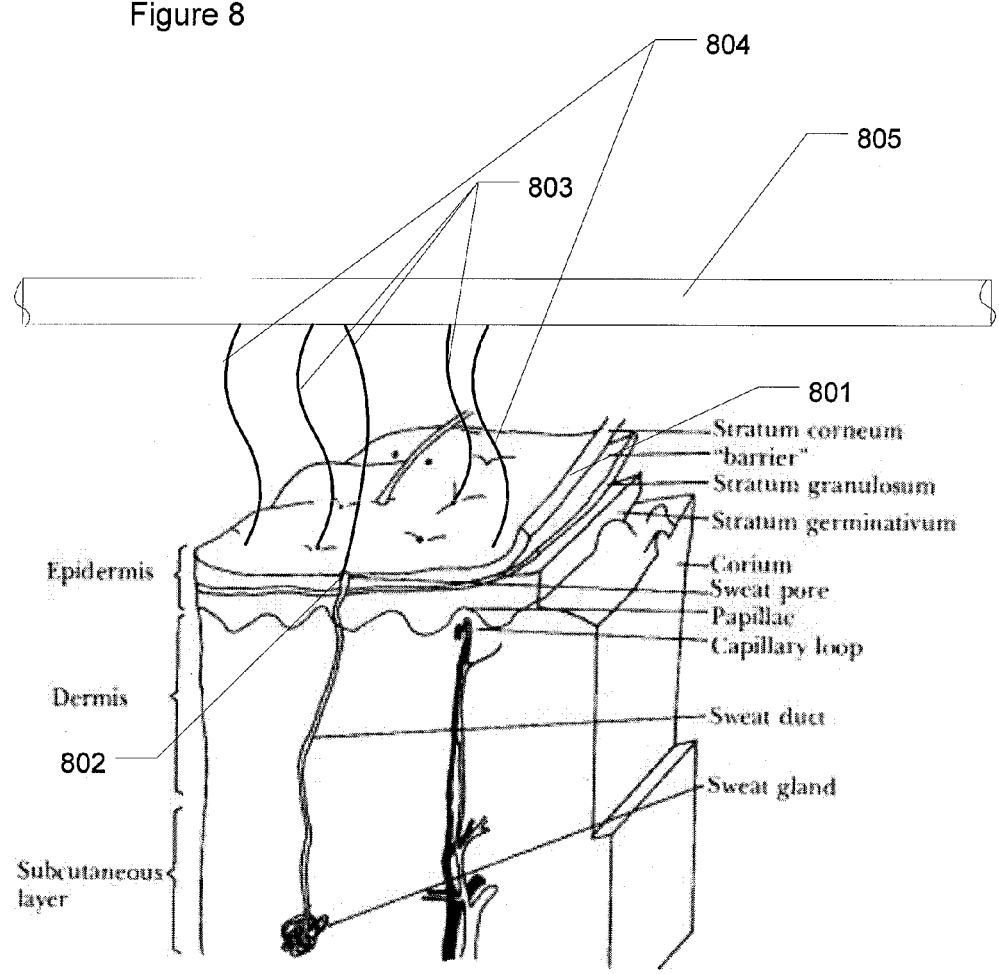

APPARATUS, SYSTEM AND METHODS FOR SENSING AND PROCESSING PHYSIOLOGICAL SIGNALS

RELATED PATENT DOCUMENT

This patent document claims the benefit under 35 U.S.C. §119 of U.S. Provisional Patent Application Ser. No. 61/432,095 filed on Jan. 12, 2011, and entitled "Electrode for Sensing Physiological Signals and Methods Therefor;" this provisional patent application is fully incorporated herein by reference.

FIELD OF INVENTION

Various aspects of the present invention relate to devices such as electrodes, and data collection and processing for monitoring physiological signals, and to incorporation of such devices into a garment that can be worn by animals or human beings for monitoring physiological signals such as those pertaining to ECG signals.

BACKGROUND

Physiological signals have been monitored for a variety of purposes. For example, ECG monitoring involves using sensing electrodes that will detect the electrical currents of the heart so they can be amplified and recorded electronically. Electrodes can be placed inside the body, under the skin, on the surface of the skin, and in the vicinity of the skin. It is often useful to obtain long term (e.g., more than a few days) recordings from ambulatory subjects. This allows recording of transient events such as arrhythmias that may only occur infrequently or under rare circumstances.

Long term ambulatory ECG monitoring is difficult to achieve without the use of an implantable monitoring device. Electrodes have often been very uncomfortable or may induce an allergic reaction, resulting in poor patient compliance. Monitoring systems incorporated into comfortable garments have provided poor quality signals; therefore, the information they provide is not adequate to facilitate good decision making as to the presence or absence of arrhythmias or other abnormalities in the ECG.

Regarding sensing electrodes, one type is a "wet" electrode that is affixed to the skin with an adhesive, and often employs a gel or electrolyte to improve electrical contact with the skin. Wet electrodes have produced high quality signals, relative to other types of electrodes available for monitoring ambulatory subjects. However, these electrodes often induce an allergic reaction when used for more than a few days, may require that the area where the electrode is applied be shaved, and are seldom tolerated by patients for more than two weeks.

Another type of sensing electrode is a "dry" electrode made of a conductive material that is positioned on the skin without using a "wet" contacting material. Although these electrodes are usually better tolerated for longer term recordings than wet electrodes, they often provide a relatively poor quality signal. Large baseline wander and loss of signal due to clipping is common with these electrodes.

In addition to issues associated with electrode design, the data collection instrumentation and signal processing systems used to collect and process signals from dry electrodes have been incapable of addressing the signal quality (e.g., baseline wander) limitations of dry electrodes. Dry electrode systems are typically only used for monitoring heart rate because of these limitations and are not considered useful for collection of diagnostic information such as arrhythmia detections.

These and other considerations have presented challenges to the detection of physiological signals, such as ambulatory ECG signals, for a variety of uses such as the assessment of arrhythmias and intervals.

SUMMARY

Various aspects of the present invention are related to devices and methods for sensing, recording, and evaluating electrocardiogram and other physiological signals in a manner that addresses the challenges described above, providing comfort and convenience for the monitored subject and a good quality signal from which to extract information.

In accordance with various example embodiments, a skin-contacting electrode includes an electrically conductive sensing sheet having a conductive surface, and conductive flexible microfibers extending from the conductive surface and configured to sense a physiological signal such as an ECG signal. Certain embodiments are directed to the implementation of such an electrode with the conductive sensing sheet contacting a subject's skin with the conductive flexible microfibers extending into the subject's skin pores, and collectively sensing an ECG signal that is communicated for analysis via the fibers and the conductive sensing sheet.

Another example embodiment is directed to an apparatus for sensing an ECG signal from a subject. The apparatus includes a skin-contacting electrode having a conductive surface and conductive flexible microfibers extending from the surface. The microfibers sense the ECG signal (e.g., via pores as discussed above) which is communicated to a signal-processing circuit communicatively coupled to the electrode. The signal-processing circuit decomposes the ECG signal from a first domain into subcomponents in a second domain, identifies at least one subcomponent corresponding to frequencies of less than 5 Hz, removes energy corresponding to baseline wander from the at least one subcomponent, and reconstructs the ECG in the first domain using at least the subcomponents from which baseline wander energy was removed.

According to another example embodiment, sensing electrodes are incorporated into the inside surface of a garment at multiple locations. The garment is fabricated of a non-conductive or poorly conductive elastic material that helps to keep the electrodes in contact with the skin, and is placed on the body at a location where acceptable signal levels of the desired physiological signal are present. Sensing electrodes are fabricated of a thin, hypoallergenic, and flexible conductive sheet. The electrode is fabricated in a manner that provides for flexible or somewhat flexible conductive microfibers extending from one side of the conductive surface in a generally perpendicular orientation to the disk. The conductive fibers in combination with pores in the conductive sheet allow the skin beneath the sensor to breathe.

In another aspect of the present invention, a conductive sheet having a sensing electrode includes a conductive polymer or aromatic material such as porous graphene and the microfibers include cross-linked chains of carbon atoms attached at the pores of the graphene.

In another aspect of the present invention, oxygen or another polar entity is bonded to at least the distal region of the microfibers in order to render at least the distal end of the fibers hydrophilic in order to improve electrical coupling between the skin and the electrode.

In another aspect of the present invention, a conductive sheet having a sensing electrode includes one or more of metal, polymer, or aromatic material, and flexible microfibers including carbon nanorods.

In another aspect of the present invention the electrode is fabricated of a flexible conductive open cell foam material. In some embodiments, the foam may be coated with a thin layer of titanium or other non-allergenic metallic element.

In another aspect of the present invention, active electrodes within an input impedance greater than 1 gigaohm and input dynamic range greater than +/−1 volt are employed that buffer and amplify the sensed ECG and transform the impedance to less than 100 ohms for wired communication to the data collection apparatus.

In another aspect of the present invention, a buffer-amplifier with a dynamic range of greater than +/−1 volt, input impedance of >1 gigaohm, and gain of about 100 is used to amplify the signal from sensing electrodes. The output of the buffer amplifier is digitized using an analog-to-digital converter with a resolution of 18 bits or greater. The digitized signal is processed to mitigate or remove baseline wander by decomposing the signal into subcomponents, applying a 0.5 to 2 Hz low-pass filter to the lowest frequency subcomponent, computing the difference between the lowest frequency unfiltered and filtered subcomponents, replacing the original lowest frequency subcomponent with the computed difference, and reconstructing the signal by applying an inverse transform to the set of subcomponents.

BRIEF DESCRIPTION OF THE DRAWINGS

The invention may be more completely understood in consideration of the following detailed description of various embodiments of the invention in connection with accompanying drawings, in which:

FIG. 7 shows a signal flow diagram of an algorithm for removing baseline wander from an ECG, in accordance with one or more example embodiments;

FIG. 8 shows a diagram of human skin with microfibers of an electrode extending into skin pores, as may be implemented in connection with one or more example embodiments.

DETAILED DESCRIPTION

Figure 1:
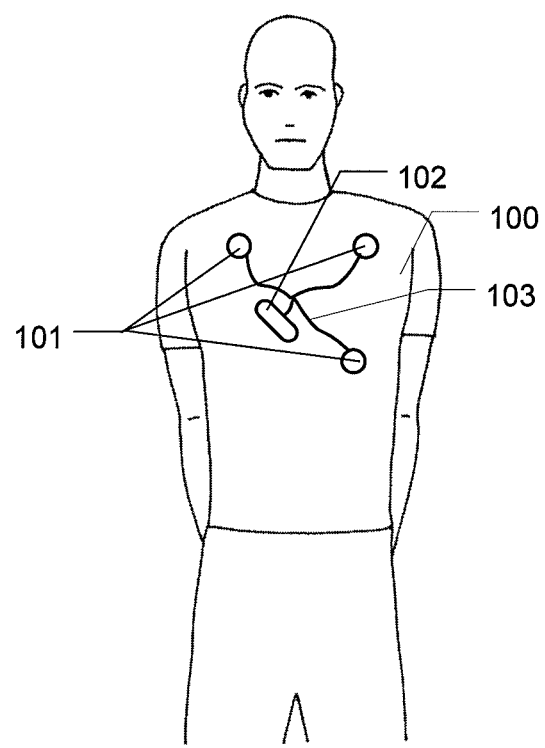
FIG. 1 shows a subject wearing an elastic shirt with ECG sensing electrodes positioned on the inner surface, consistent with one or more example embodiments of the present invention.

Various example embodiments of the present invention relate to a system, which may be incorporated into or used with a wearable garment, for sensing, collecting, and processing physiological signals at the skin surface, such as for sensing ECG signals. While the present invention is not necessarily limited to such applications, various aspects of the invention may be appreciated through a discussion of examples using this context.

Various embodiments of the present invention are directed to aspects of an apparatus or system including sensing electrodes in contact with the surface of the skin, and data collection instrumentation and signal processing algorithms (and their implementation) for removing noise and extracting useful information from the acquired signals. The apparatus/system is suitable for incorporation into a garment or other item worn by a monitored subject. Information provided may be useful for obtaining a clinical diagnosis of a patient, for managing medications and other therapies of a patient, for patient wellness purposes, for assessing the effects of an experimental therapy, and for athletic training.

Electrodes and electrode devices in accordance with embodiments as discussed herein may be implemented in a variety of manners, such as by incorporating the electrode into an elastic garment, band, or other apparatus that maintains sensing electrode contact with the skin. The sensing electrode has characteristics that provide for good electrical coupling with the skin surface. In various embodiments, good signal quality and electrical coupling between the skin and electrode is achieved without the need for special skin preparation (e.g., abrasion, alcohol wipe, or shaving). This can be especially useful when monitoring ECG signals for diagnosis and patient management, in which details regarding atrial and ventricular activity are important to making a proper diagnosis and evaluating therapies.

In accordance with various embodiments, an electrode device is fabricated of materials that are inert and hypoallergenic, comfortable to wear, and designed to breathe in order to avoid trapping moisture under the electrode that could result in skin irritation.

Certain embodiments of the present invention are directed to monitoring subjects for long periods of time (e.g., weeks or months). In various contexts, one or more embodiments are directed to addressing challenges to wearable electrodes, such as those discussed in the background above in connection with both wet and dry electrodes. In some embodiments, electrodes as discussed herein are dry electrodes implemented using a conductive surface that is placed in contact with the skin. Such electrodes may be implemented without gel, an electrolyte or other fluid that enhances electrical contact. Electrodes can be incorporated into belts and straps, or into garments by selective placement of conductive fibers in a stretchable garment or by attaching conductive surfaces (e.g., fabricated of a conductive substance), inside a stretchable garment.

In a more particular example embodiment, a skin-contacting electrode for measuring physiological signals includes an electrically conductive sensing sheet having a conductive surface, and conductive flexible microfibers extending from the conductive surface. The sheet is configured and arranged to contact a subject's skin, and the flexible microfibers can be used to facilitate the sensing of a physiological signal, such as an ECG signal. The size of the sensing sheet can be tailored to suit particular applications, and in some applications has a diameter of between about 10 to 30 mm.

In some implementations, the flexible microfibers exhibit flexibility to extend into respective skin pores to facilitate the sensing of a physiological signal. For instance, different microfibers may extend generally perpendicular from the electrode and, when contacted to a subject's skin, flexibly bend to enter differently-oriented pores and obtain a physiological signal via the pores. This approach facilitates the sensing of physiological signals via the pores, which can be less insulating than other portions of the skin.

In these and other contexts, a flexible microfiber refers to a fiber that readily bends, but has a tendency to remain straight when not subjected to forces that cause it to flex such that different microfibers may bend to enter different skin pores of a subject undergoing analysis (e.g., for ECG sensing). In some implementations, such flexible microfibers are configured to sense an ECG signal via the different skin pores without penetrating the skin. In this context, such flexible microfibers may have insufficient stiffness to penetrate the skin, such as to penetrate an insulating-type layer (e.g., the horny layer) of skin for sensing an ECG signal.

Accordingly, in some embodiments, different ones of the conductive flexible microfibers are respectively configured and arranged to flexibly bend in different directions to enter a plurality of differently-oriented skin pores of a subject and sense the ECG signal therefrom.

The microfibers may include a variety of materials, such as cross-linked carbon chains attached at the pores of such a graphene material. In some embodiments, the microfibers include polar structures attached to the distal end of the microfiber, with the polar structures (e.g., which may include oxygen) rendering the microfibers hydrophilic. In other embodiments, the microfibers include t-butyl groups attached to carbon chains and the t-butyl groups orient the microfibers along a direction that is about perpendicular to a surface of the conductive sheet (absent compressive force). The flexible microfibers respectively bend in different directions to protrude into differently-oriented skin pores and sense a physiological signal therefrom.

Other materials and combinations are used for the electrode, to suit certain embodiments. Some embodiments are directed to an electrode having a conductive surface including a graphene material with microfibers including or consisting of one or more of carbon nanotubes and graphene ribbons.

In a more particular embodiment, an apparatus having an electrode as discussed above includes a garment of substantially non-conducting elastic fabric (e.g., a fabric such as spandex or elastane), and the electrode is affixed to the inside of the non-conducting fabric to sense ECG of the subject.

Another example embodiment is directed to an apparatus for sensing an ECG signal from a subject. The apparatus includes a skin-contacting electrode and a signal-processing circuit. The electrode has a conductive surface that contacts the subject's skin, and conductive flexible microfibers extending from the conductive surface to sense the ECG signal. The signal-processing circuit is communicatively coupled to the electrode and removes baseline wander by decomposing the ECG signal from a first domain into subcomponents in a second domain, identifying at least one subcomponent corresponding to frequencies of less than 5 Hz, removing energy corresponding to baseline wander from the at least one subcomponent, and reconstructing said ECG in the first domain using at least the subcomponents from which baseline wander energy was removed.

In some embodiments, removing energy corresponding to baseline wander from the at least one subcomponent involves high-pass filtering the subcomponent. In other embodiments, removing the energy includes low pass filtering at least one subcomponent to estimate a baseline wander waveform, computing at least one difference value by subtracting the baseline wander waveform from the at least one subcomponent, and replacing said at least one subcomponent with said at least one difference value.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

Turning now to the Figures, FIG. 1 shows sensing electrodes 101 attached to the inner surface of shirt 100, in accordance with an example embodiment Shirt 100 is fabricated of an elastic mostly non-conductive fabric such as spandex or elastane. The sensing electrodes may be attached to the fabric using one or more approaches such as those including the use of an adhesive, rivets, or stitching. In one embodiment, sensing electrodes are 1 to 3 cm in diameter and are porous to allow moisture on the skin surface to evaporate. Sensing electrodes are electrically connected to monitoring electronics module 102 via insulated conductors 103.

In some embodiments, the electronics module 102 contains electronics to amplify and digitize the sensed signals and also contains a computing component. The computing component is configured/programmed to remove baseline wander and noise, extract information, compress useful information, and communicate that information via a wireless communication link to a computerized system or display where the information can be reviewed or otherwise processed as appropriate. In other embodiments, the electrode has an integral active element that provides a gain of from 1 to 100 and an input impedance of >1 gigaohm.

Various aspects of the system are useful in mitigating the effects of baseline wander. These include characteristics of the electrodes that lead to a more stable interface with the skin, front-end buffer-amplifier characteristics that lead to less baseline wander, and analog-to-digital converter characteristics that allow the system to tolerate a large baseline wander without compromising ECG signal information. Further, in connection with one or more of these or other embodiments, it has been discovered that baseline wander may be mitigated or removed using an approach involving a decomposition of a signal to subcomponents. A subcomponent identified as containing baseline wander is manipulated to identify a waveform corresponding to baseline wander. The estimate is then subtracted from the identified subcomponent (or otherwise unused) to compute a modified subcomponent with baseline wander removed. An inverse transform is then applied to a set of subcomponents, including the modified subcomponent and the remaining subcomponents, to reconstruct the original signal with substantially suppressed baseline wander.

Figure 2A:
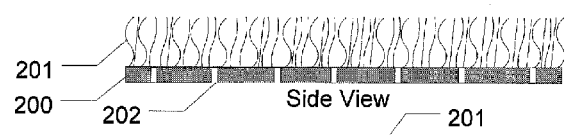
FIG. 2A and FIG. 2B respectively show side and top views of the construction of an electrode, consistent with another example embodiment of the present invention.
Figure 2B:
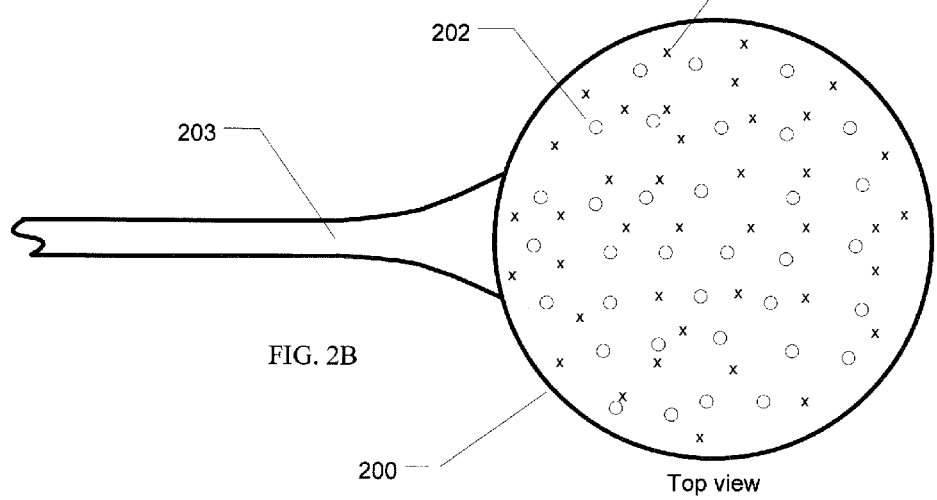

FIG. 2A and FIG. 2B respectively show side and top views of an electrode sensing surface constructed of a thin flexible sheet 200 with a conductive surface, in accordance with other example embodiments. In one embodiment, the conductive sheet is a disk approximately 1 to 3 cm in diameter, although electrodes of other shapes and sizes are implemented with other embodiments. Flexibility of the sheet is such that it can easily conform to the contours of the body surface in order to maximize percentage of area in contact with the skin. In one embodiment, sheet 200 contains numerous small pores 202 of less than 500 microns in diameter through which moisture secreted by the skin (e.g., sweat) can breathe and evaporate. Attached to the disk are conductive microfibers 201 that, as an example, have a diameter ranging from 1 to 200 microns.

In some embodiments, microfibers 201 protrude from the disk a sufficient distance to protrude into openings in a layer of dead skin (e.g., and positioning around hair on the skin) to improve the electrical coupling of the electrode with the skin. The density of microfibers 201 is high enough that the likelihood of several fibers making good electrical contact with the skin is high, but the density is low enough that the microfibers can pass between body hairs to make contact with the skin.

In one embodiment, microfibers 201 as discussed above extend 250 to 2500 micrometers from the disk and the density of the fibers is 100 to 5000 per square cm. Other fiber lengths and densities may also be useful. In some embodiments, the fiber length and density is set based upon the subject from which physiological signals are being obtained, and the location on the subject (e.g., abdomen, thorax, sides, shoulders, etc.) from which the signals are acquired.

In some embodiments, the microfibers 201 are sufficiently flexible that they are perceived as soft and non-irritating to the subject to which the electrode is applied, but sufficiently stiff that they tend to project perpendicular to the disk except when deformed during compression. In some embodiments, the microfibers are fabricated of a material that will maintain a tendency toward extending perpendicular from flexible sheet 200. This lasting "spring" or "resiliency" property is maintained in a moist or dry environment such that if they are compressed against the skin, they will return to a roughly perpendicular orientation to the conductive sheet when compression is released. The electrode materials that are in skin contact are fabricated of hypoallergenic materials to mitigate or avoid skin irritation and allergic reactions. In some embodiments, the electrode and system electronics is washable in a standard consumer washing machine.

In some embodiments, insulated conductor 203 is fabricated of the same material as the disk and is electrically insulated with insulating tubing or by a coating of insulating material such as parylene. In another embodiment, a braided stainless steel insulated conductor is electrically connected to disk 200 using a conductive adhesive, such as silver filled epoxy resin from Master Bond (East Greenbush, N.Y.), or it may be attached with a conductive rivet.

There are a number of materials from which the microfibers 201 can be fabricated to provide the desirable properties of electrical conductivity, biocompatibility/nonallergenic, an appropriate degree of flexibility, ability to spring back to a roughly perpendicular orientation following compression of the electrode against the skin, and durability. These materials may be selected according to these terms, and for a particular application. Microfibers 201, for example, could be fabricated of a conductive polymer, conductive aromatic (e.g., graphene), carbon nanotubes, or various forms of metalized polymers, or metallic materials.

In many embodiments, the microfibers 201 are sufficiently flexible to mitigate or inhibit invasive interaction with a subject. For example, devices that penetrate into a subject's living skin or other tissue may be uncomfortable. In this context, microfibers 201 are configured to be sufficiently flexible to be comfortable for the patient, but also sufficiently resilient or rigid to penetrate skin hair and self-position in skin pores and openings in the horny layer of the skin in order to maintain good electrical contact.

Figure 3:
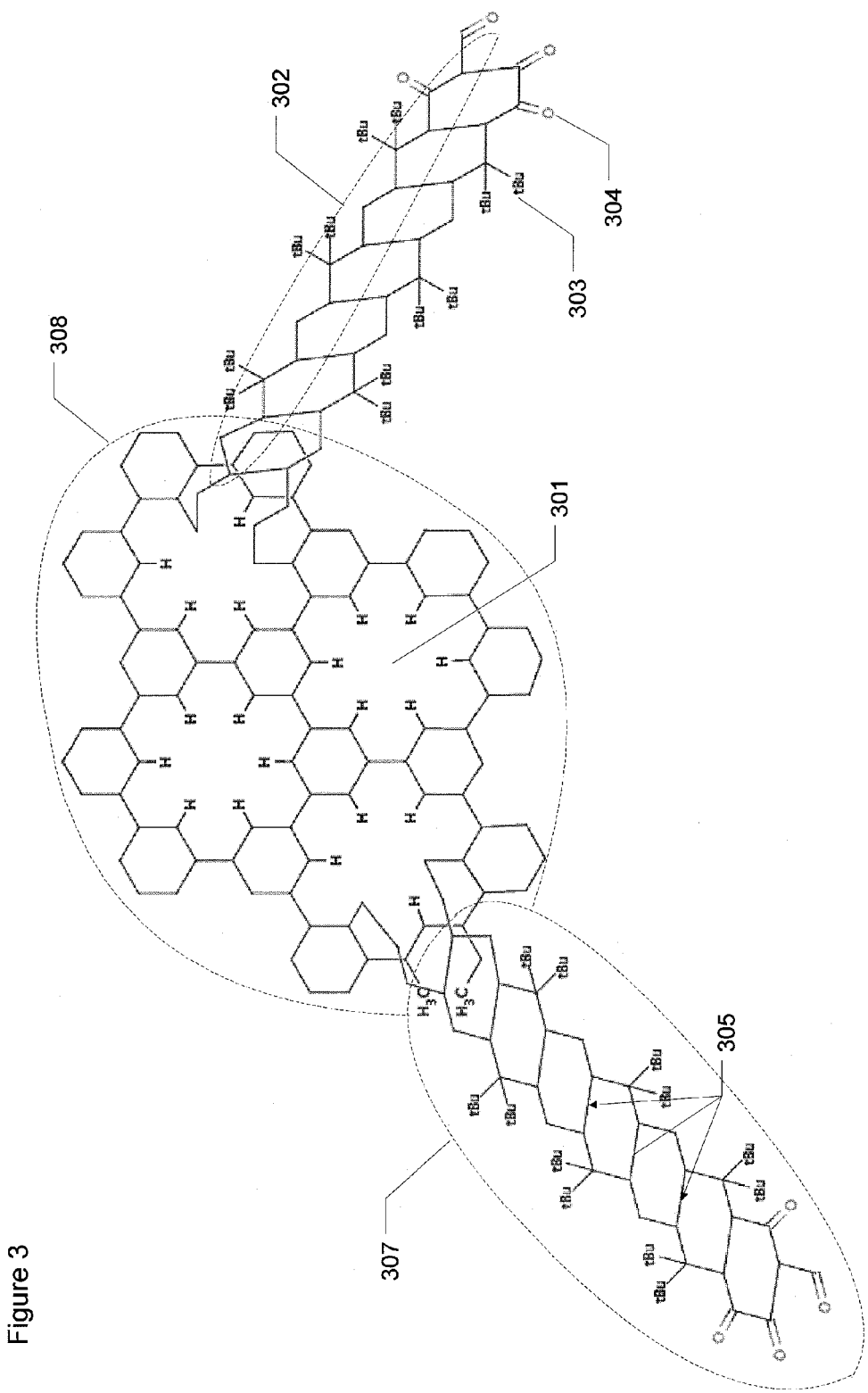
FIG. 3 shows a representation of the chemical structure of an embodiment of an electrode, consistent with another example embodiment of the present invention.

FIG. 3 shows a skin-contacting surface of a conductive sheet including multilayer graphene, for use with an electrode as discussed herein, in accordance with other example embodiments. In one embodiment, the graphene is porous. Both porous and non-porous graphene are highly conductive, with an electrical resistivity on the order of $10^{-6}$ Ohm-cm, less than the resistivity of silver [1]. Both porous and non-porous graphene are strong and can be fabricated as a very thin flexible multilayer sheet [2]. The chemical structure of porous graphene sheet 308 includes some "pores" 301 with bonded hydrogen atoms. These atoms can be replaced with other bonds, such as long carbon chains 302 containing cross-links 305 with another carbon chain to form conductive microfibers 307. By using hydrogen atoms already present within the porous graphene structure, microfibers 307 are interspersed without disrupting the functionality and overall structure of graphene sheet 308. The structures in FIG. 3 are shown to represent the chemical structure only and not the actual size. Upon implementation in a sensing element, graphene sheet 308 and microfibers 307 would contain several orders of magnitude more molecular entities than is shown in FIG. 3.

In one embodiment, to render the carbon microfibers sufficiently resilient, carbon chains are cross-linked at points 305. The number of carbon chains that will be cross-linked in each microfiber in order to achieve acceptable mechanical properties is at least several thousand. Rigidity and tendency of the carbon microfibers toward a perpendicular orientation to conductive sheet 308 can be further manipulated by bonding large entities 303 to the carbon chains. In one embodiment, these large entities are t-butyl groups.

In another embodiment, the microfibers that project from conductive sheet surface include conductive carbon nanotubes. In another embodiment, the microfibers 307 include ribbons of a material with a porous or non-porous graphene surface. The porous graphene surface may be useful in order to provide sites for attachment of polar entities 304 for hydrophilicity and for attaching entities to control physical properties such as resiliency of the microfibers and hence tendency to maintain a perpendicular orientation to conductive sheet 308.

In some embodiments, polar entities such as oxygen atoms 304 are attached at or near the distal end of the microfibers 307 to render at least the distal portion hydrophilic. When the subject perspires, the moisture in the skin will loosely bond with the surface of the fiber to improve the electrical coupling between the fiber and the skin. This may be especially useful when the monitored subject is exercising heavily and exhibiting a high degree of movement. In those situations, movement artifacts can be particularly troublesome, and the coupling with the skin in accordance with these embodiments can be used to mitigate such artifacts and improve signal quality. In one embodiment, polar entities 304 are bonded to the long-chain carbon entities and in another embodiment polar entities 304 are bonded to carbon nanotubes.

Figure 4:
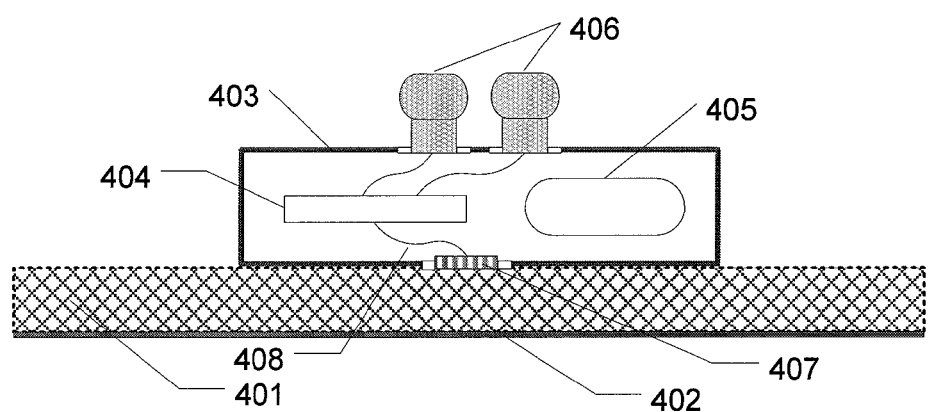
FIG. 4 shows a drawing of an active electrode, consistent with another example embodiment of the present invention.

In another embodiment, referring to FIGS. 1 and 4, electrodes 101 are fabricated of conductive foam 401. In one embodiment, conductive foam electrode 401 is 1 to 3 cm in diameter and is fabricated of 1 to 10 mm thick open cell polyurethane foam having a resistivity of 500 to 5,000 ohms per square. Open cell foam has the advantage of presenting an irregular surface which can improve electrical contact with the skin and can also be highly flexible to provide comfort for the subject wearing the monitoring device. In some embodiments, the foam is coated with a 100 nm to 10,000 nm thick conductive layer 402 that is substantially more electrically conductive than foam 401 and improves electrical contact with the skin. Conductive layer 402 is composed of a material that is hypoallergenic and inert and can be deposited on the foam material at a temperature that will not damage the properties of foam. In one embodiment conductive layer 402 is titanium deposited using a low-temperature pressure vapor deposition process. In another embodiment, conductive layer 402 is of gold.

In another embodiment, electrodes 101 are active electrodes. The ECG signal is sensed from the tissue via conductive layer 402 and foam 401, and is electrically connected from foam 401 to buffer-amplifier 404 via bond 407 and wire 408. An electrical reference connection and output for buffer-amplifier 404 is provided via connector 406. Battery 405 provides power for buffer-amplifier 404. In one embodiment, bond 407 is achieved using conductive epoxy. In one embodiment, buffer-amplifier 404 has an input impedance of >1 gigaohm, a DC leakage current of <100 pico-amp, and an output impedance of <100 ohm. In some embodiments, housing 403 provides electromagnetic interference (EMI) shielding for buffer-amplifier 404 and connections to foam 401. In one embodiment, housing 403 is constructed of metallic sheet material. In another embodiment, housing 403 is constructed of a metallized plastic such as is available from Cybershield (Lufkin, Tex.). The buffer-amplifier 404 is configured, arranged and/or implemented with a very high input impedance and low leakage current to reduce baseline wander during subject movement and to reduce the need for skin preparation prior to placing the electrode on the skin. Positioning the amplifier at the electrode allows the connections from the electrode to the buffer-amplifier to be very short and reduces the complexity and cost of shielding the high-impedance connections and circuits from EMI.

A challenge of obtaining useful high-quality information from ECGs obtained from ambulatory subjects is that the resistance of the tissue-electrode interface can change significantly with movement of the subject. This is especially true of dry electrodes. Accordingly, various embodiments are further directed to the improvement in signal quality and information extracted from electrodes, using various data collection instrumentation and signal processing algorithms employed in combination with the electrode designs described herein. By combining improvements in electrode performance, data collection instrumentation, and signal processing algorithms, system performance can be improved over the state-of-the-art to provide higher quality information from ECGs of ambulatory subjects.

Figure 5:
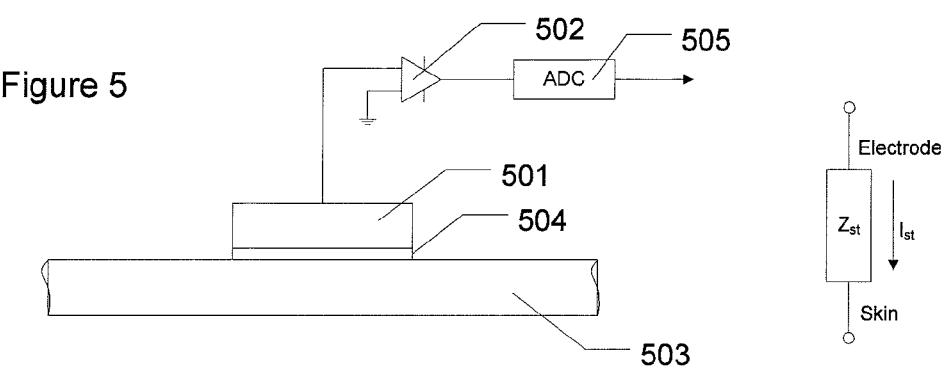
FIG. 5 shows a block diagram of a sensor and front-end electronics for sensing, buffering, amplifying, and digitizing an ECG, suitable for incorporation into a wearable garment in connection with one or more example embodiments.

Referring to FIG. 5, the tissue-electrode interface 504 can, in its simplest form, be represented by impedance $Z_{st}$ through which a current $I_{st}$ flows (e.g., between electrode 501 and skin 503). The current $I_{st}$ includes a combination of currents generated by the body $I_b$ (e.g., electrical activity of the heart) and the DC offset current $I_o$ generated by the buffer-amplifier 502 and converted via ADC 505. $I_o$ is >>than $I_b$ and therefore $I_{st} \approx I_o$. As the subject moves, causing a change in the tissue-electrode interface impedance $Z_{st}$, a shift in base line proportional to $I_o * Z_{st}$ occurs. If, for example, $I_o$ is 1 nano-Amp and a movement of the electrode relative to the skin results in a 100 megaohm change in $Z_{st}$, a corresponding 100 mV baseline shift at the input of 502 would occur. Various embodiments are directed to mitigating or eliminating monitoring aspects in which this change in $Z_{st}$ would cause the front-end amplifier to hit the rail, cause the signal to be clipped, and lose signal information.

In an embodiment of the present invention, the DC offset current $I_o$ of buffer-amplifier 502 is <100 pico-Amperes (pA), the gain is 100, and the dynamic range is +/−1 volt. In some instances, DC offset is <10 pA. If a 100 M-ohm change in $Z_{st}$ occurred as a result of movement when $I_o$ was 100 pA, a baseline shift of 1 volt would occur at the output of buffer-amplifier 502 as a result of the 100 M-ohm change in $Z_{st}$. This deviation during baseline shift would remain within the dynamic range of 502 and therefore clipping and information loss would be avoided. The relative low gain (e.g., 100), however, may create an issue of resolution of the ECG signal that is riding on the baseline. During normal operation, the amplitude of the voltage sensed by electrodes 101 would be about 1 mV, corresponding to a 100 mV change in the output of buffer-amplifier 502. Analog-to-digital converters (ADC) used to digitize ECG in ambulatory monitoring devices may not designed to provide sufficient resolution given that the amplitude of the ECG is much less than the dynamic range of buffer-amplifier 502. In one embodiment of the present invention this issue is addressed by using an 18-bit or higher resolution ADC in order to achieve sufficient resolution for processing the ECG and accommodate the dynamic range required to avoid clipping during large fluctuations in baseline voltage during subject movement. In some implementations, this approach is also implemented to mitigate or eliminate the need to have an adjustable dynamic range, as an 18 bit or higher resolution ADC would accommodate most/all signal amplitude ranges and still provide adequate resolution to preserve signal information in ambulatory monitoring devices. Mitigating or eliminating the need for an adjustable gain of the monitoring device simplifies use for the customer and avoids data loss from an inappropriate gain setting. In some embodiments, it may be useful for buffer-amplifier 502 to have a +/−3 volt dynamic range in order to accommodate even wider fluctuations in $Z_{st}$ during subject movement. In this and other embodiments, it may be useful for the ADC to have a resolution of 20 bits or greater.

The various computing components, circuits and signal processing methods described herein can be implemented using a variety of devices and methods. For example, logic or processing circuits can be implemented using one or more of: discrete logic circuitry, fully-programmable and semi-programmable circuits such as PLAs (programmable logic arrays), specialized processors or general purpose processors that are specially programmed. Combinations of these and other circuit components are also possible and within the scope of various embodiments, including those discussed above. For example, the computing component in electronics module 102 of FIG. 1 can be implemented in a variety of circuit-based forms, such as through the use of data processing circuit modules. Such systems are exemplified by implementation in high-speed programmable computer/processor circuits, or in combination with discrete and or semi-programmable circuitry (e.g., as Field-Programmable Gate Arrays, Programmable Logic Devices/Arrays).

Figure 6:
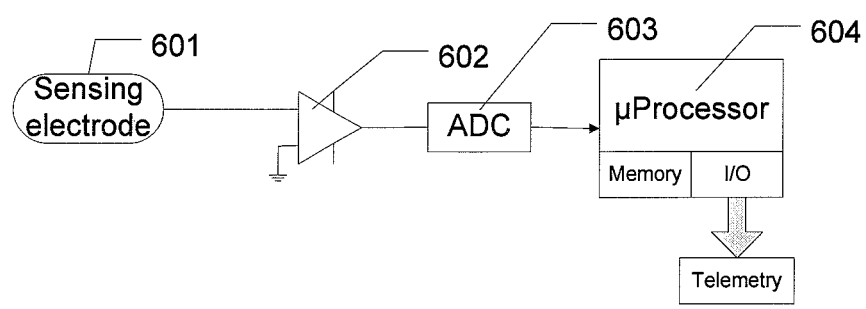
FIG. 6 shows a block diagram of a system for sensing, collecting, denoising, and extracting information from ECGs, in accordance with one or more example embodiments.

In one embodiment, referring to FIG. 6, ECG sensing electrodes 601, located on or near the skin of the monitored subject, are electrically connected to buffer-amplifier 602 having an input impedance of >1 gigaohm, DC leakage current of <100 pA, dynamic range of about +/−1 volt, and gain of 100. The output of buffer-amplifier 602 is electrically connected to analog-to-digital converter 603, ADC 603 having a resolution of >18 bits. A signal processing algorithm implemented in microprocessor 604 processes the digitized ECG to remove baseline wander and other noise to produce a denoised ECG signal. In some embodiments, microprocessor 604 also implements algorithms for extracting information such as intervals (e.g., QT interval, QRS duration) from the denoised ECG signal.

An enhanced method for baseline wander removal can be implemented to achieve further improvement of signal quality and accuracy of information extracted from the ECG. In one embodiment, referring to FIG. 7, an input ECG signal 701 in the first domain is decomposed at block 702 into subcomponents $D2_{sub1} \ldots D2_{subN}$, $D2_{subL}$ in a second domain. In one embodiment, decomposition is achieved using one of a discrete cosine transform or a wavelet transform. The subcomponent with the lowest frequency content $D2_{subL}$, selected in step 703, contains information from low-frequency ECG waves (e.g., T wave), baseline wander, and other low-frequency signals such as respiration. A waveform corresponding to the baseline wander is estimated by low-pass filtering $D2_{subL}$ in step 704 with a frequency cut-off (e.g., 3 dB down) between 0.05 to 2 Hz to produce a signal LPF ($D2_{subL}$). In one embodiment, the low-pass filter (LPF) is an IIR filter such as a Butterworth filter. In another embodiment, the LPF is an FIR filter. The estimated baseline waveform LPF ($D2_{subL}$) is subtracted from $D2_{subL}$ in step 705. The difference, D2subF, is the subcomponent $D2_{subL}$ with baseline wander removed and replaces $D2_{subL}$. The ECG signal with baseline wander removed is then reconstructed from the set of subcomponents $D2_{sub1} \ldots D2_{subN}, D2_{subF}$ in step 706 by applying an inverse of the transform used for decomposition, and can be output at block 707.

In an alternate embodiment, steps 704 and 705 are replaced by a step whereby a high-pass filter (HPF) is applied to subcomponent $D2_{subL}$ to remove the baseline wander. In one embodiment, the cutoff frequency of the high-pass filter is between 0.05 and 2 Hz. In one embodiment, the high-pass filter is an Infinite Impulse Response (IIR) filter such as a Butterworth filter. In another embodiment the HPF is an FIR filter.

In another embodiment, the digitized signal output from ADC 603 is high-pass filtered to remove baseline wander. In some applications, where preservation of T-wave morphology may not be important but it is desired to preserve QRS energy, frequency cut-off (−3 dB relative to pass-band) can be between 1 to 5 Hz. In another embodiment, the signal is post-processed to identify isoelectric points between the end of T and start of P wave. The baseline is estimated by interpolating over the isoelectric points. The estimated baseline is then subtracted from the ECG. In another embodiment an adaptive filter can be used to remove baseline wander. The simultaneously collected impedance signal can serve as a reference signal for the adaptive filter.

In some embodiments, aspects of the baseline wander can contain useful information. For example, certain changes in baseline wander commonly occur as a result of changes in thoracic impedance with ribcage movement and lung inflation during respiration. In one embodiment the estimated baseline wander calculated in step 704 is further processed to extract respiration parameters such as respiratory rate, inspiratory time, and expiratory time. In one embodiment, extraction of respiratory parameters includes low-pass filtering of the estimated baseline wander to remove non-respiratory related artifacts. In one embodiment, when extracting respiratory parameters from a human ECG and mammals larger than about 10 kg, the estimated baseline wander is low-pass filtered with a cutoff of 1 to 2 Hz. The output of the low-pass filter is processed to detect either positive or negative zero crossings to indicate onset, peak, and offset of the respiratory cycle. Onset, peak, and offset information can be used to compute respiratory rate, inspiratory time, and expiratory time. In another embodiment the QRS amplitude changes and RR interval changes are included in the algorithm to improve the accuracy of respiration rate calculation.

FIG. 8 shows a representative diagram of human skin with microfibers of an electrode extending into skin pores, as may be implemented in connection with one or more example embodiments. Referring to FIG. 1 by way of example, electrode 101 may be implemented as shown in FIG. 8, in position on the skin. The outer surface of the skin is comprised of flat keratinous material that forms the stratum corneum 801, or horny layer of dead tissue. The outer layer 801, compared to the underlying skin layers such as the *stratum granulosum* and *stratum germinativum*, is more electrically resistive. When using wet electrodes, it is common to remove at least a portion of the horny layer 801 by abrading the skin, which can be used improve electrical contact between a sensing electrode and the underlying tissue (e.g., to make the sensing of ECG signals possible under certain conditions). Various embodiments herein are directed to sensing such physiological signals, without necessarily abrading or otherwise penetrating the skin. Pores 802 pass from the skin surface through the horny more resistive layer 801 and are used to access to the underlying more conductive layers of the skin. Conductive microfibers 803 and 804 extend from the surface of conductive sheet 805. Some of the microfibers may contact horny layer 801, as is the case with microfibers 804, which exhibit a highly resistive electrical contact with the skin if horny layer 801 is in place. Other microfibers, such as 803, make contact with the pores in the skin, provide an improved electrical contact with the underlying tissue, and hence improve the quality of the sensed ECG. Those microfibers 803 that contact the inner surface of pores 802 bypass the higher resistance of horny layer 801, thereby improving tissue-electrode contact without taking additional steps in skin preparation such as abrasion. In addition, the flexibility of the microfibers permits the application of the electrode against the skin, with some microfibers entering pores at different orientations, and some microfibers that do not enter pores bending (perhaps even flat) against the skin to permit the close positioning of the electrode and entry of the other microfibers into the pores.

The garment referenced in the preceding descriptions can take several forms, as the various apparatuses (e.g., electrodes and/or sensing circuitry), systems and methods herein may be implemented with a multitude of disparate garments to suit particular needs. For monitoring ECG signals, the garment shown in FIG. 1 is placed on the thorax. Garment 100 can consist of a t-shirt comprised of elastic material, or it can consist of an elastic band or multiple elastic bands that surround the chest with electrodes 101 located on the inner surface. In one embodiment, garment 100 is fabricated of an elastic material with minimal tendency to absorb water and is woven in a "fishnet" pattern to facilitate air movement at the skin and faster drying time should the garment be exposed to water or sweat. In one embodiment the openings in the fishnet pattern range from 1/16 to 3/16 inch. In another embodiment, electrodes are fabricated of materials whereby sensing performance and electrode integrity is not negatively affected by water, such as any of the electrode materials previously proposed herein for use as dry electrodes. In some embodiments, electronics module 102 is housed in a sealed water-tight housing such as a high-density polyethylene housing with seams that are bonded with adhesive or with heat. Adhesives suitable for bonding include hot melt adhesives that are formulated for bonding polyethylene or epoxy adhesives that are applied to an appropriately prepared surface to facilitate adhesion. Bonding seams with heat can be accomplished by ultrasonic welding, for example. To eliminate the need to access the battery in housing 102, and hence eliminate a potential path for water ingress, a rechargeable cell is employed along with magnetic or RF field recharging circuitry. The combination of use of a garment material that is will not absorb water, electrodes that are not negatively impacted by water, an electronics housing that is water-tight, and a wirelessly rechargeable power source contained within electronics module 102 allows the patient to shower without the need to remove the garment and monitoring apparatus. This capability can save substantial nursing labor when the garment is used to monitor patients in a hospital environment, allows more robust monitoring regimens (e.g., patient can be monitored while showering), and is more convenient and comfortable for the patient. The fishnet style also has benefits for use in fitness monitoring and other applications where diaphoresis is an issue, as it facilitates evaporation of sweat from the skin faster and keeps the subject more comfortable.

In one embodiment, a garment is used to monitor fetal ECG and uterine EMG. In this embodiment, the garment may be in the form of an elastic band that covers a substantial portion of the abdomen and underlying uterus. In this embodiment, the band may incorporate twelve or more electrodes.

It should be recognized that aspects of the electrode designs, buffer-amplifier and ADC designs, and signal processing algorithm for removing baseline wander discussed here can also be useful when monitoring subcutaneous ECG. For example, the electrode embodiments described herein having conductive microfibers extending generally perpendicular from a conductive surface can be configured to permit and/or encourage extensive tissue ingrowth around the microfibers, thereby increasing the tissue electrode surface area and hence improving the stability of the electrical contact with the tissue. The buffer-amplifier characteristics, ADC characteristics, and the algorithm for removing baseline wander described herein are also beneficial for use in a subcutaneous device to address baseline wander issues and eliminate the need for a gain setting adjustment.

Based upon the above discussion and illustrations, those skilled in the art will readily recognize that various modifications and changes may be made to the present invention without strictly following the exemplary embodiments and applications illustrated and described herein. For example, different types of electrodes and electrode materials may be used. In addition, a variety of different types of fabrics and other materials that are used to hold or house electrodes may be used. Moreover, such items may be formed to, and used in connection with, interaction with various parts of a patient, for both human and animal physiological signal detection. Still other embodiments are directed to methods of sensing physiological signals, as may be implemented with aspects described herein. Such modifications do not depart from the true spirit and scope of the present invention, including that set forth in the following claims.

REFERENCES

1. Akturk, A. and Goldsman, N. (2008) "Electron transport and full-band electron phonon interactions in graphene" J. of Applied Physics 103.
2. Allen, M., Tung, V., Kaner, R. (2010) "Honey Carbon: A Review of Graphene" Chem. Rev. 110:132-145.

What is claimed is:

1. A skin-contacting electrode apparatus for measuring ECG signals, the apparatus comprising:
   an electrically conductive material; and
   conductive flexible microfibers extending from the conductive material, and configured and arranged to protrude into pores in skin and sense an ECG signal from inner surfaces of the pores, below a surface layer of the skin in which the pores reside.

2. The apparatus of claim 1, wherein different ones of the conductive flexible microfibers are respectively configured and arranged to flexibly bend in different directions to enter a plurality of differently-oriented skin pores of a subject and sense the ECG signal therefrom.

3. The apparatus of claim 2, wherein the conductive flexible microfibers are configured and arranged to sense the ECG signal from ones of the conductive flexible microfibers protruding into the skin pores without penetrating the skin, and the conductive flexible microfibers include:
   a first one of the conductive flexible microfibers that is configured and arranged to extend into a first one of the plurality of differently-oriented skin pores having a first orientation,
   a second one of the conductive flexible microfibers that is configured and arranged to extend into a second one of the plurality of differently-oriented skin pores having a second orientation while the first one of the conductive flexible microfibers extends into the first one of the plurality of differently-oriented skin pores, and
   a third one of the conductive flexible microfibers that is configured and arranged with the first and second conductive flexible microfibers to flexibly bend against an outer surface of the subject's skin while the first and second conductive flexible microfibers extend along different orientations into the first and second ones of the plurality of differently-oriented skin pores.

4. The apparatus of claim 3, wherein the conductive flexible microfibers have insufficient stiffness to penetrate the skin.

5. The apparatus of claim 1, wherein the conductive material includes a graphene material and the conductive flexible microfibers consist of carbon nanotubes.

6. The apparatus of claim 1, wherein the material includes a graphene material and the conductive flexible microfibers consist of graphene ribbons.

7. The apparatus of claim 1, wherein the material includes a graphene material and the conductive flexible microfibers include carbon nanotubes.

8. The apparatus of claim 1, wherein the material includes a graphene material and the conductive flexible microfibers include graphene ribbons.

9. The apparatus of claim 1, wherein the conductive material is a flexible disk having a diameter of between about 10 to 30 mm.

10. The apparatus of claim 1, further including a garment of substantially non-conducting elastic fabric, wherein the electrically conductive material is affixed to an inside portion of the non-conducting fabric to sense the ECG signals.

11. The apparatus of claim 1, wherein the conductive flexible microfibers are configured and arranged to, in the absence of compressive force, extend in a direction that is about perpendicular to the conductive material.

12. The apparatus of claim 1, wherein the conductive flexible microfibers are configured and arranged to collect the ECG signal without penetrating the skin.

13. A skin-contacting electrode for measuring physiological signals, the electrode comprising:
   an electrically conductive sensing material having a conductive surface; and
   conductive flexible microfibers extending from the conductive surface and including first microfibers and second microfibers, the first microfibers being configured and arranged to detect the physiological signals by
      extending into a plurality of pores in skin of a subject at different orientations while the second microfibers flexibly bend along a surface of the skin, and
      detecting the physiological signals via interior surface areas of the pores below a surface layer of the skin in which the pores reside and having low insulating characteristics, relative to insulating characteristics of a surface area of the skin from which the pores are recessed, using the first microfibers while the second microfibers flexibly bend along the surface of the skin.

14. An apparatus for sensing an ECG signal from a subject, the apparatus comprising:

a skin-contacting electrode having
a conductive surface, and
conductive flexible microfibers extending from the conductive surface and configured and arranged to protrude into pores in skin and to sense the ECG signal from inner surfaces of the pores, below a surface layer of the skin in which the pores reside and
a signal-processing circuit communicatively coupled to the electrode and configured and arranged to remove baseline wander by:
decomposing the ECG signal from a first domain into subcomponents in a second domain,
identifying at least one subcomponent having energy corresponding to baseline wander,
removing the energy corresponding to baseline wander from the at least one subcomponent, and
reconstructing said ECG in the first domain using at least the subcomponents from which the energy corresponding to baseline wander was removed.

15. The apparatus of claim 14, wherein removing the energy corresponding to baseline wander from the at least one subcomponent includes high-pass filtering said at least one subcomponent.

16. The apparatus of claim 14, wherein removing energy corresponding to baseline wander from the at least one subcomponent includes
low pass filtering the at least one subcomponent to estimate a baseline wander waveform,
computing at least one difference value by subtracting the baseline wander waveform from the at least one subcomponent, and
replacing said at least one subcomponent with said at least one difference value.

17. An apparatus comprising:
an electrically conductive material having a conductive surface that includes a porous graphene material; and
conductive flexible microfibers that include cross-linked carbon chains attached at the pores of the graphene material, the conductive flexible microfibers extending from the conductive surface and being configured and arranged to protrude into skin pores and sense an ECG signal.

18. The apparatus of claim 17, wherein each of the conductive flexible microfibers includes polar structures attached to a distal end of the microfiber, with a proximal end of each microfiber being coupled to the conductive surface, the polar structures being configured and arranged to render the conductive flexible microfibers hydrophilic.

19. The apparatus of claim 18, wherein the polar structures include oxygen.

20. The apparatus of claim 17, wherein the conductive flexible microfibers include t-butyl groups attached to the carbon chains and the t-butyl groups are configured and arranged to orient the conductive flexible microfibers along a direction that is about perpendicular to the conductive surface.

21. An apparatus comprising:
an electrically conductive sensing material having a conductive surface including a porous graphene material; and
conductive flexible microfibers that include cross-linked carbon chains attached at the pores of the graphene material, the conductive flexible microfibers extending from the conductive surface and including first microfibers and second microfibers, the first microfibers being configured and arranged to detect physiological signals by
extending into a plurality of pores in skin of a subject at different orientations while the second microfibers flexibly bend along a surface of the skin, and
detecting the physiological signals via interior surface areas of the pores having low insulating characteristics, relative to insulating characteristics of a surface area of the skin from which the pores extend, using the first microfibers while the second microfibers flexibly bend along the surface of the skin.

22. The apparatus of claim 21, wherein each of the conductive flexible microfibers includes polar structures attached to a distal end of the conductive flexible microfiber, with a proximal end of the conductive flexible microfiber being coupled to the conductive surface, the polar structures being configured and arranged to render the conductive flexible microfibers hydrophilic.

23. The apparatus of claim 22, wherein the polar structures include oxygen.

24. The apparatus of claim 21, wherein the conductive flexible microfibers include t-butyl groups attached to the carbon chains and the t-butyl groups are configured and arranged to orient the microfibers along a direction that is about perpendicular to the surface absent compressive force, and the conductive flexible microfibers are configured and arranged to respectively bend in different directions to protrude into differently-oriented skin pores and sense the physiological signal therefrom.

* * * * *